United States Patent [19]

Takamatsu

[11] 4,349,014
[45] Sep. 14, 1982

[54] ENDOSCOPE SYSTEM

[75] Inventor: Takeshi Takamatsu, Hachioji, Japan

[73] Assignee: Olympus Optical Co., Ltd., Tokyo, Japan

[21] Appl. No.: 190,609

[22] Filed: Sep. 25, 1980

[30] Foreign Application Priority Data

Oct. 2, 1979 [JP] Japan .................................. 54-127004

[51] Int. Cl.³ .............................................. A61B 1/06
[52] U.S. Cl. .......................................... 128/6; 128/3; 364/413; 354/62
[58] Field of Search ........................................ 128/3–9, 128/11, 13, 18, 303.1; 364/413, 416; 354/62, 145

[56] References Cited

U.S. PATENT DOCUMENTS

| | | |
|---|---|---|
| 3,599,630 | 9/1980 | Sato . |
| 4,024,866 | 5/1977 | Wallach .......................... 364/413 X |
| 4,086,583 | 4/1978 | Takahashi ............................ 354/62 |
| 4,153,356 | 9/1980 | Hama . |
| 4,180,812 | 12/1979 | Kaltenbach et al. ............. 433/28 X |
| 4,204,528 | 5/1980 | Termanini ......................... 354/62 X |
| 4,310,228 | 1/1981 | Terada ................................ 128/6 X |

Primary Examiner—Gene Mancene
Assistant Examiner—Mickey Yu
Attorney, Agent, or Firm—Frishauf, Holtz, Goodman & Woodward

[57] ABSTRACT

An endoscope system includes an endoscope, light source unit and photographic attachment are connected to a centralized supervision-control device which collectively supervises and controls the overall operating condition of the endoscope, light source unit and photographic attachment.

7 Claims, 9 Drawing Figures ered nonconducting. After a prescribed length of
ENDOSCOPE SYSTEM

BACKGROUND OF THE INVENTION

This invention relates to an endoscope system comprising at least an endoscope and a light source unit.

An endoscope system has recently been developed into a multifunction type. Hitherto, a plurality of exclusive control devices were provided to attain the multifunction object. As the functions increased in number, control devices occupied a large percentage of volume relative to the volumes of the implements constituting an endoscope system, that is, an endoscope, light source unit and endoscope photographic attachment. Moreover, the constituent implements had a complicated arrangement, readily leading to the failures and erroneous behaviors of the endoscope system as a whole. Moreover, the prior art endoscope system was not provided with a device for collectively supervising and controlling the operating condition of the various constituent implements and in some cases discovering their faults. As a result, the conventional endoscope system was accompanied with the drawback that a failure to quickly detect the appearance of an accident in the endoscope system gave rise to the possibility of exposing a patient to an unexpected risk.

It is accordingly the object of this invention to provide an endoscope system which can be collectively supervised in a single place for control.

SUMMARY OF THE INVENTION

To attain the above-mentioned object, this invention provides a centralized supervision-control device designed to collectively supervise at least an endoscope and light source unit for control of their operation. The centralized supervision-control device is connected to the endoscope and light source unit by an electric signal-transmitting line.

DETAILED DESCRIPTION

Figure 1:
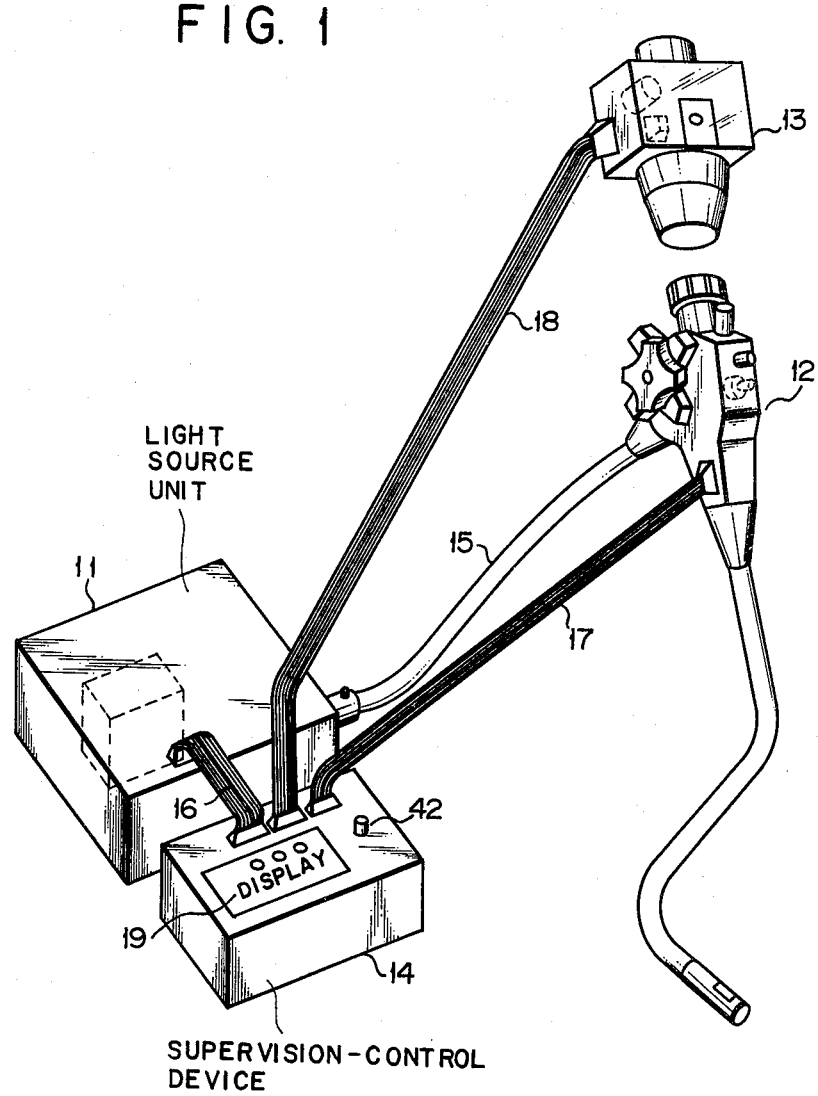
FIG. 1 is an oblique view of an endoscope system according to a first embodiment of this invention.

An endoscope system according to a first embodiment shown in FIG. 1 comprises a light source unit 11, endoscope 12 and endoscope photographic attachment 13. This endoscope system is further provided with a centralized supervision-control device 14. The endoscope 12 is connected to the light source unit 11 through a universal cord 15. The endoscope photographic attachment 13 is fitted to the eyepiece section of the endoscope 12. The centralized supervision-control device 14 is connected to the light source unit 11, endoscope 12 and photographic attachment 13 through the corresponding signal transmission lines 16, 17, 18. The centralized supervision-control device 14 is provided with a display device 19 for indicating the overall operating condition of the whole endoscope system.

Figure 2:
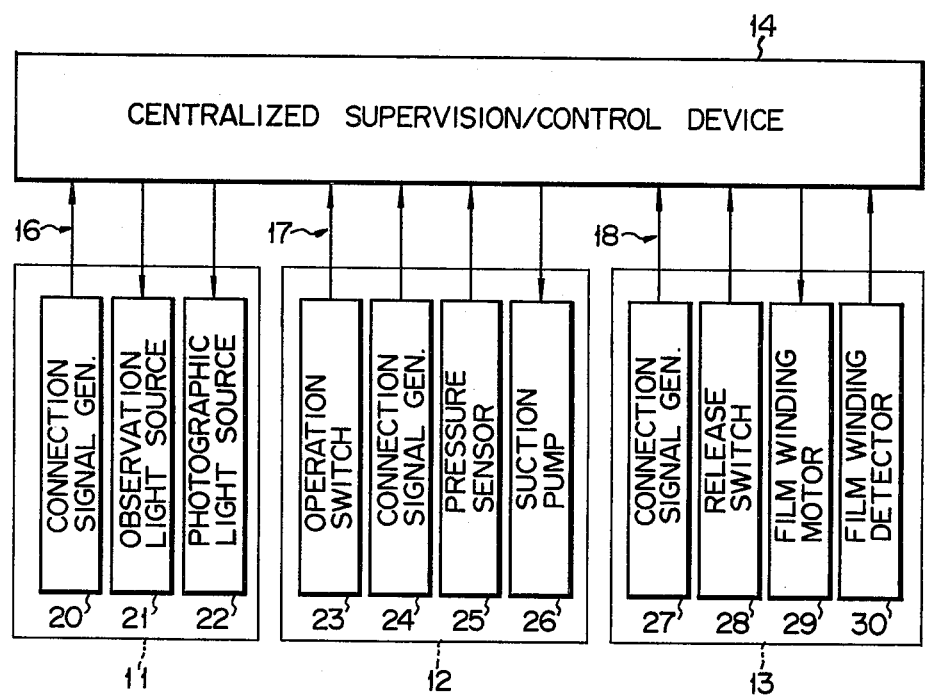
FIG. 2 shows the circuit arrangement of the main part of the endoscope system according to the first embodiment of FIG. 1.

As seen from FIG. 2, the light source unit 11 is provided with a connection signal generator 20, observation light source 21 and photographing light source 22. These elements are connected to the centralized supervision-control device 14 through the signal transmission line 16. The endoscope 12 comprises an operation switch 23, connection signal generator 24, pressure sensor 25 and suction pump 26. The photographic attachment 13 comprises a connection signal generator 27, release switch 28, film-winding motor 29 and film-winding detector 30.

Figure 3:
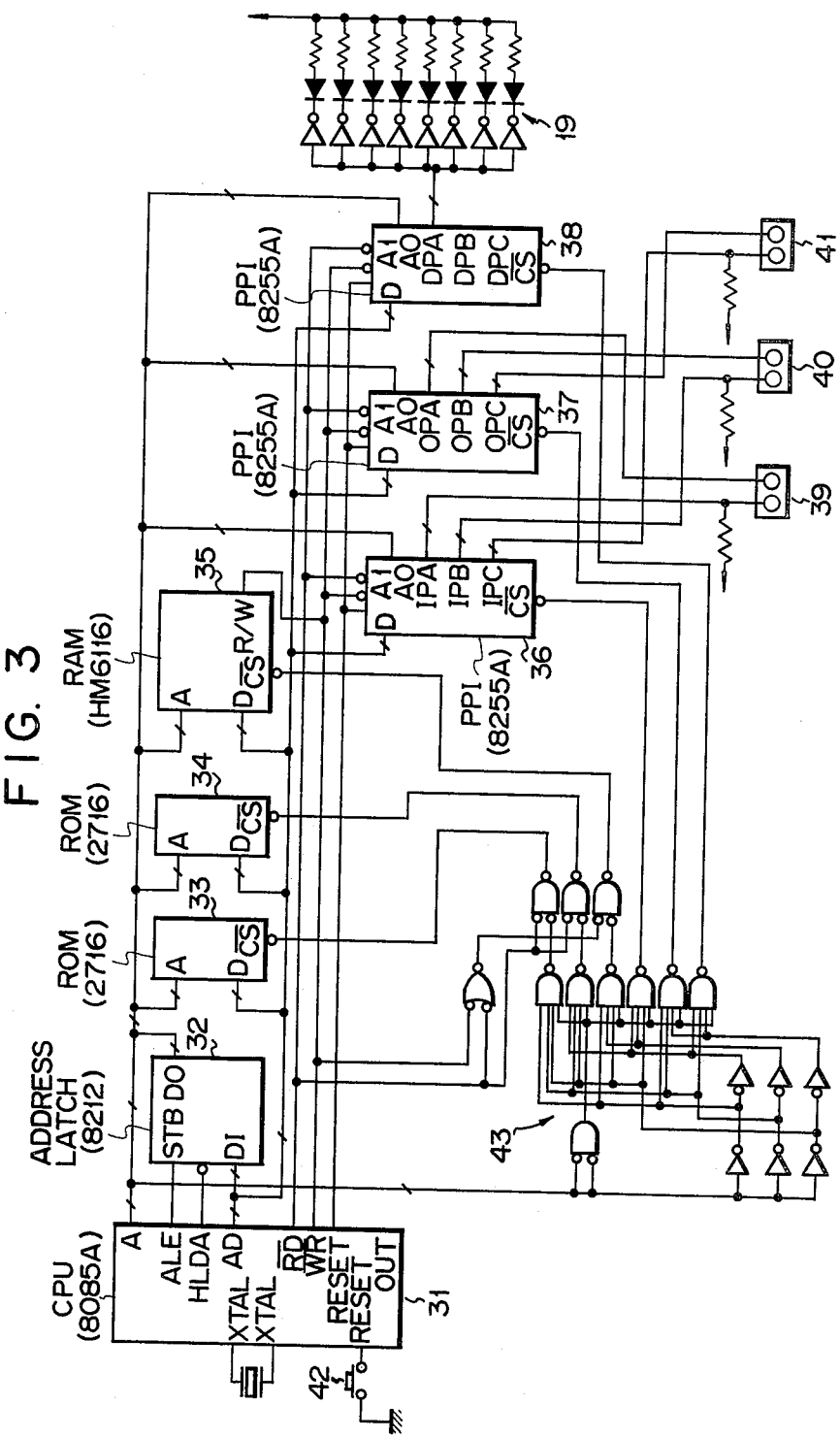
FIG. 3 sets forth the circuit arrangement of the centralized supervision-control device of FIGS. 1 and 2.
Figure 4:
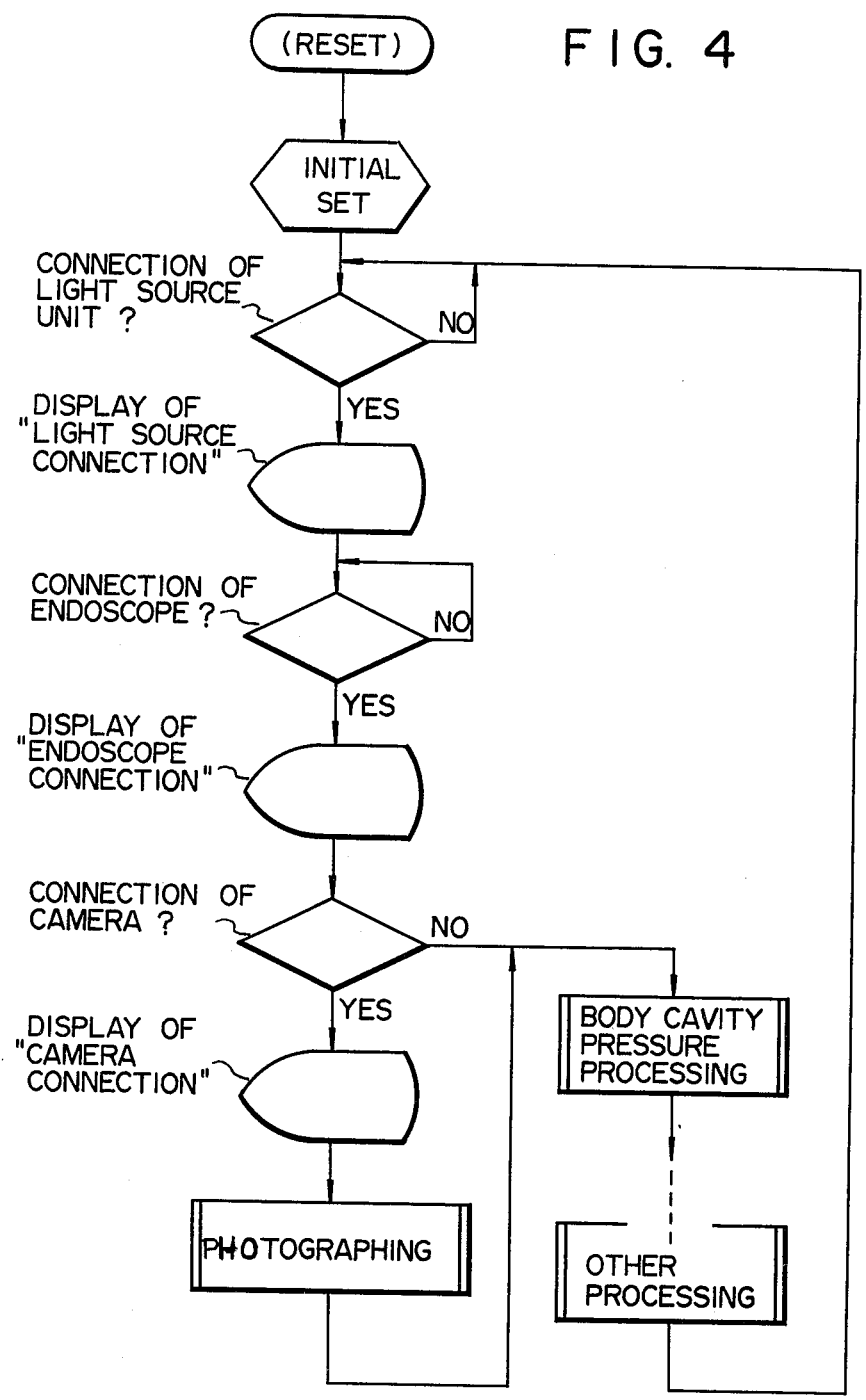
FIGS. 4 to 7 are flow charts showing the operation of the subject endoscope system.
Figure 5:
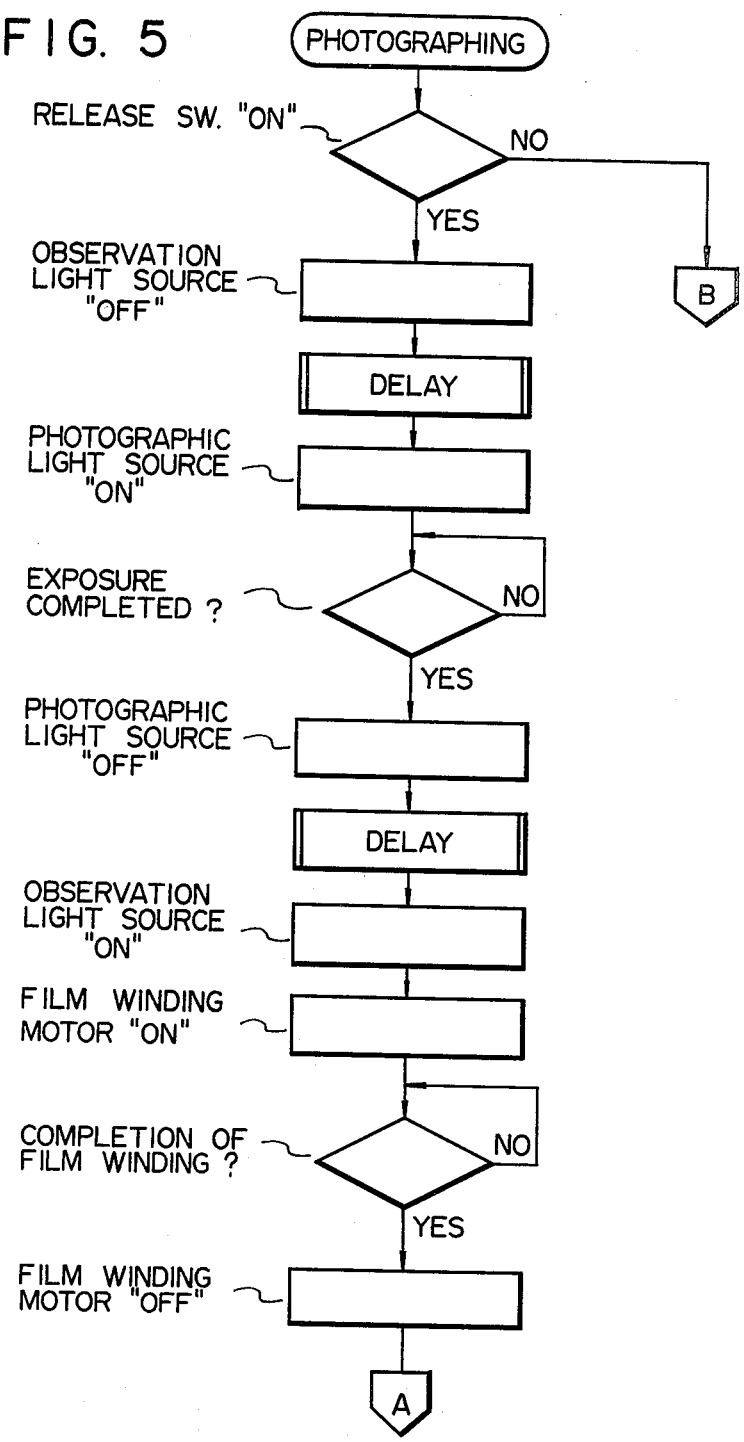
Figure 6:
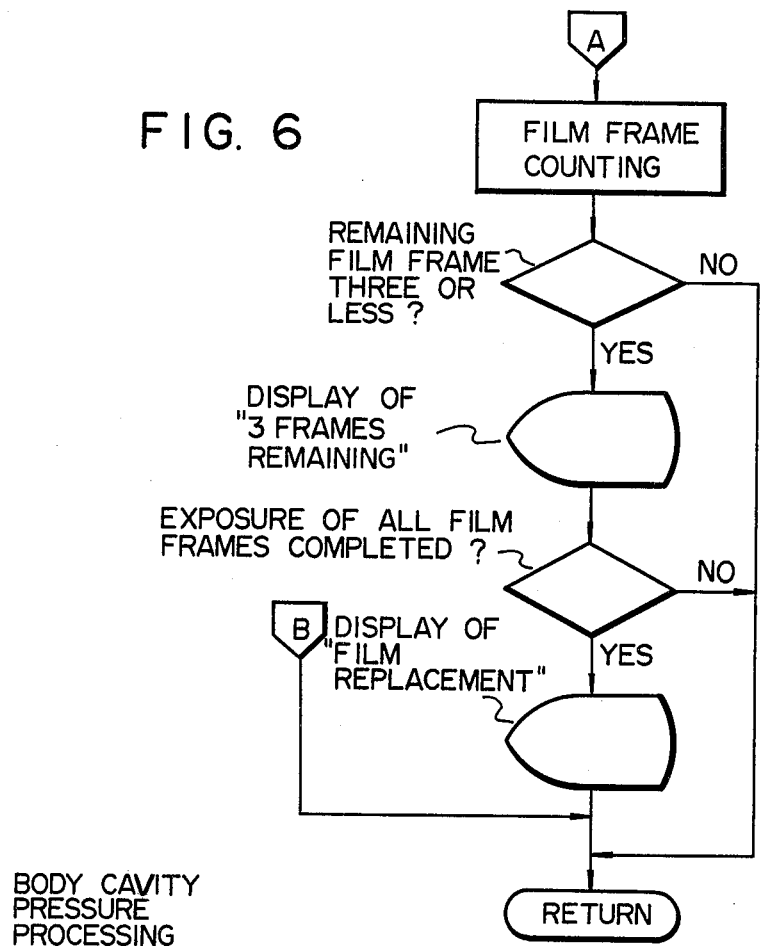
Figure 7:
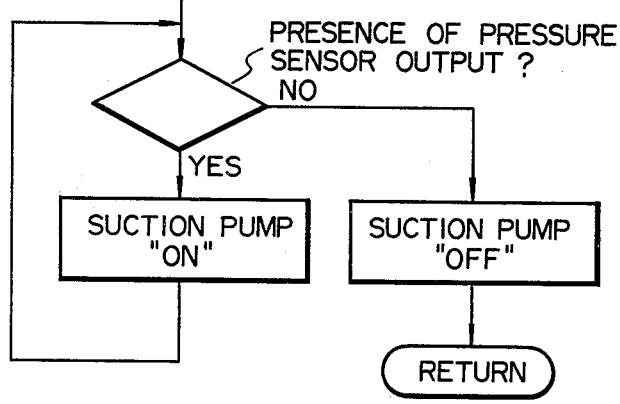

The integrated supervision-control device 14 comprises, as shown in FIG. 3, CPU (intel 8085A) 31, address latch circuit (intel 8212) 32, ROM (intel 2716) 33, ROM (intel 2716) 34, RAM (intel HM 6116) 35 and programmable peripheral interfaces (intel 8255A) 36, 37, 38. The terminals IPA, IPB, IPC of PPI 36 are respectively connected to one of the terminals of each of the corresponding connectors 39, 40, 41. The reset input terminal of CPU 31 is connected to a reset switch 42. A reset output terminal is connected to the reset terminals of PPI 36, 37, 38. The read terminal RD and write terminal WR of CPU 31 are connected to the corresponding terminals of PPI 36, 37, 38. The terminal A of CPU 31 is connected to the terminal A of ROM 33, 34 and RAM 35 respectively, and also to a logic circuit 43. The terminal AD of CPU 31 is connected to the terminal DI of the address latch 32 and the terminals D of ROM 33, 34, RAM 35, PPI 36, 37, 38. The terminal DPA of PPI 38 is connected to the display device 19.

Description is now given with reference to the flow charts of FIGS. 4 to 7 of the operation of an endoscope system embodying this invention. When the reset switch 42 of the centralized supervision-control device 14 is actuated, then the device 14 is brought to an initial set position CPU 31 sends forth an inquiry signal to find whether the light source unit 11 is connected to a connector 39. Where the light source unit 11 is connected to the connector 39, then CPU 31 orders through PPI 38 the display device 19 to make an indication "Light Source Connection" in response to an output signal from the connection signal generator 20 of the light source unit 11. When it is found upon an inquiry by CPU 31 that the endoscope 12 is connected to the connector 40, then CPU 31 orders the display device 19 to make an indication "Endoscope Connection". When the photographic attachment 13 is connected to the connector 41, than the display device 19 makes an indication "Photographic Attachment Connection". When, under this condition, the coeliac cavity is photographed, CPU 31 determines whether a release switch (not shown) is actuated or not. When recognizing the actuation of the release switch, CPU 31 causes the observation light source 21 of the light source unit 11 to be rendered nonconducting. After a prescribed length of time, the photographic light source 22 of the light source unit 11 emits light. The emitted light illuminates a foreground subject through a light guide (not shown). Light reflected from the foreground subject exposes a film of the photographic attachment 13 through an image guide (not shown) of the endoscope 12. An amount of irradiated light is calculated, for example, by an exposure meter (not shown) set in the light source unit 11. When detecting that a proper amount of light has been emitted, the centralized supervision-control device 14 renders the photographic light source 22 nonconducting. After a prescribed length of time, the observation light source is rendered conducting. At this time, the film winding motor 25 is driven to start the takeup of a film. The completion of the takeup of the film is detected by the film winding detector 30. The film winding motor 25 is stopped in response to an output detection signal from the film winding detector 30. At this time, a number of exposed film frames is counted. Determination is made as to whether three or fewer film frames remain unexposed. Where less than three film frames remain unexposed, the display device 19 makes an indication "3 Frames Remaining". Later when it is detected that all the film frames have been exposed, then the display device 19 makes an indication "Film Replacement".

The coeliac cavity is photographed as described above. Description is now given of the manner in which the coeliac pressure is supervised and controlled. Air or water is introduced into the coeliac cavity. The coeliac pressure is detected by a pressure sensor 25 disposed at the distal end of the insertion section of the endoscope 12. A signal denoting a detected coeliac pressure is transmitted to the centralized supervision-control device 14. Where a detected coeliac pressure is found to be higher than a predetermined level, then the centralized supervision-control device 14 actuates a suction pump 26 to reduce a coeliac pressure. Where a prescribed coeliac pressure is reached, the suction pump 26 is stopped.

As described above, this invention causes the overall operation condition of the constituent members of an endoscope system, that is, a light source unit, endoscope and endoscope photographic attachment to be collectively supervised and controlled by a centralized supervision-control device. Therefore, it is unnecessary to provide a control device for the respective constituent members of the endoscope system. Further, any abnormal operation of the endoscope system can be detected easily and quickly, enabling counter-measures to be immeidately taken against the fault.

Figure 8:
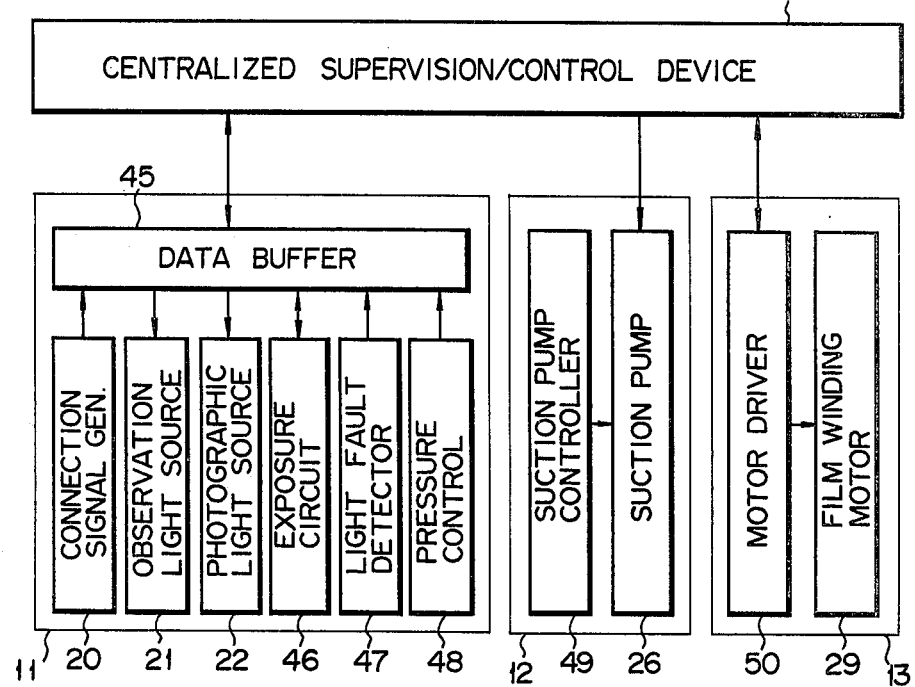
FIG. 8 indicates the circuit arrangement of the main part of an endoscope system according to a second embodiment of the invention.

Description is now given with reference to FIG. 8 of an endoscope system according to a second embodiment of this invention. The light source unit 11 is provided with a data buffer 45, which is connected to the connection signal generator 20. Observation light source 21, photographic light source 22, exposure circuit 46, light fault detector 47 and pressure control 48. The endoscope 12 is provided with a suction pump controller 49. Under the normal condition, a suction pump 26 is controlled by a suction pump controller 49. Where the controller 49 falls, then the centralized supervision-control device 14 controls the suction pump 26. The film winding motor 29 of the photographic attachment 13 is driven by a motor driver 50, which in turn is controlled by the centralized supervision-control device 14.

With the second embodiment of FIG. 8, data transmission between the light source unit 11 and centralized supervision-control device 14 is bidirectionally effected by means of the data buffer 45. The light fault detector 47 detects the failure of the photographic light source 22. The failure is indicated on the display device 19 of the centralized supervision-control device 14, informing the operator that it is impossible to photograph a coeliac cavity.

Figure 9:
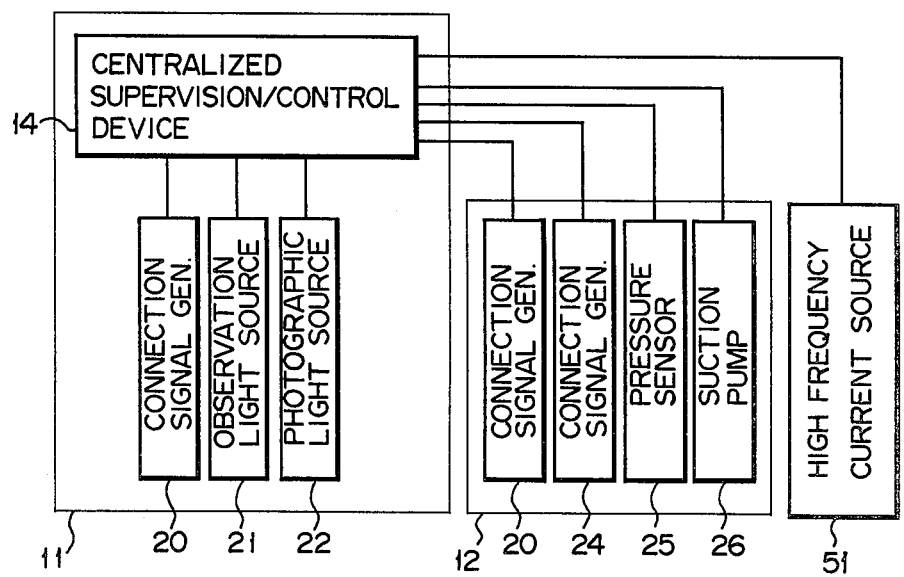
FIG. 9 shows the circuit arrangement of the main part of an endoscope system according to a third embodiment of the invention.

Referring to FIG. 9 showing the circuit arrangement of an endoscope system according to a third embodiment of this invention, the light source unit 11 is provided with the centralized supervision-control device 14, which controls the respective main sections of the light source unit 11, endoscope 12, peripheral device, for example, a power source 51 for a high frequency scalpel device. When the high frequency current of the power source 51 for the high frequency scalpel device happens to leak, then this leakage is detected by the centralized supervision-control device 14, thereby suppressing the generation of the high frequency current.

As described above, the operating condition of an endoscope system embodying this invention is collectively supervised and controlled in a single place, making it unnecessary to provide a plurality of exclusive control devices for the various inplements used to attain the multifunction object. When a failure arises in an endoscope system, the centralized supervision-control device of this invention suppresses the subsequent occurrence of a fault or accident in the endoscope system, thereby elevating its reliability. Further, the operating condition of the constituent members of the endoscope system is collectively displayed in one place, allowing for the easy recognition of the operating condition. A further advantage of this invention is that it is unnecessary to provide many control devices, allowing for the miniaturization of the constituent members of the endoscope system and ensuring a prominent improvement on their operating efficiency.

A signal transmission line used in the foregoing embodiments may be formed of a wire, optical fiber or sound-transmitting medium. Further, the transmission of a signal may be effected by any of the full duplex transmission system, half duplex transmission system and unidirectional transmission system. Moreover, the transmission of a signal may be made by wire or by a wireless system.

What is claimed is:

1. An endoscope system comprising:
an endoscope including a light guide; an image guide; an eyepiece section; and an endoscope connection signal generator for generating an endoscope connection signal;
a light source unit including a light source for conducting light to the light guide of the endoscope; and a light source unit connection signal generator for generating a light source unit connection signal;
a photographic attachment including means for connection to the eyepiece section of the endoscope to photograph a coeliac cavity; and a photographic attachment connection signal generator for generating a photographic attachment connection signal;
a centralized supervision-control unit for supervising and controlling the operation and interaction of the endoscope, light source unit and photographic attachment with respect to each other; and
signal transmission lines for electrically connecting the centralized supervision-control unit to the endoscope, to the light source and to the photographic attachment to thereby transmit the respective connection signals to the centralized supervision-control unit and to perform data-transmission between the centralized supervision-control unit and the endoscope, light source unit and photographic attachment, said centralized supervision-control unit supervising and controlling in response to the connection signals the operation and interaction of the endoscope, light source and photographic attachment.

2. The endoscope system according to claim 1, wherein the centralized supervision-control unit is located in the light source unit.

3. The endoscope system according to claim 1, wherein the light source unit further includes a data buffer, through which a bidirectional data transmission is carried out between the light source unit and the centralized supervision-control unit.

4. The endoscope system according to claim 1, wherein the endoscope includes a suction pump and suction pump controller, the signal transmission line between the endoscope and the centralized supervision-control device being coupled to the suction pump controller; and the suction pump is selectively actuated by the suction pump controller and centralized supervision-control unit.

5. The endoscope system according to any one of claims 1, 2, 3 or 4, wherein the centralized supervision-control unit includes display means for indicating the overall operating condition of the endoscope, light source unit and photographic attachment.

6. The endoscope system according to claim 4, wherein the endoscope includes a pressure sensor; and the centralized supervision-control unit includes means for controlling the operation of the suction pump in accordance with the magnitude of pressure detected by the pressure sensor.

7. The endoscope system according to claim 5, wherein the light source unit includes a light fault detector for detecting a fault in a light source; and the centralized supervision-control unit includes means for causing an indication "light fault" to be made by the display means in response to an output from the light fault detector.

* * * * *